US010660951B2

(12) United States Patent
Wu et al.

(10) Patent No.: US 10,660,951 B2
(45) Date of Patent: May 26, 2020

(54) ANTIBODY RECOGNIZING ARBITRARILY DESIGNED EPITOPE OF THREE OR MORE AMINO ACID RESIDUES IN A PEPTIDE AND METHOD OF GENERATING THEREOF

(71) Applicants: Zhiwei Allen Wu, Jiangsu (CN); Xilin Wu, Jiangsu (CN)

(72) Inventors: Zhiwei Allen Wu, Jiangsu (CN); Xilin Wu, Jiangsu (CN)

( * ) Notice: Subject to any disclaimer, the term of this patent is extended or adjusted under 35 U.S.C. 154(b) by 40 days.

(21) Appl. No.: 13/621,626

(22) Filed: Sep. 17, 2012

(65) Prior Publication Data

US 2014/0079735 A1    Mar. 20, 2014

(51) Int. Cl.

| | |
|---|---|
| A61K 39/00 | (2006.01) |
| A61K 39/12 | (2006.01) |
| A61K 39/21 | (2006.01) |
| A61K 39/245 | (2006.01) |
| A61K 38/00 | (2006.01) |

(52) U.S. Cl.
CPC .............. *A61K 39/21* (2013.01); *A61K 39/12* (2013.01); *C12N 2740/16034* (2013.01); *C12N 2740/16134* (2013.01); *C12N 2760/16034* (2013.01); *C12N 2770/24234* (2013.01)

(58) Field of Classification Search
CPC ................ A61K 39/12; A61K 2039/53; A61K 2039/545; A61K 2039/55505; A61K 2039/55577
See application file for complete search history.

(56) References Cited

U.S. PATENT DOCUMENTS

2010/0291145 A1    11/2010    Humphreys et al.

FOREIGN PATENT DOCUMENTS

| WO | 9511701 A1 | 5/1995 | |
|---|---|---|---|
| WO | 9511998 A1 | 5/1995 | |
| WO | WO 95/11998 * | 5/1995 | ............... C12Q 1/70 |
| WO | 2009046984 A1 | 4/2009 | |

OTHER PUBLICATIONS

Goodenow, et al. HIV-1 Isolates Are Rapidly Evolving Quasispecies: Evidence for Viral Mixtures and Preferred Nucleotide Substitutions. Journal of Acquired Immune Deficiency Syndromes. 1989. 2(4): 344-352.*
Zehender, et al. Compartmentalization of Hepatitis C Virus Quasispecies in Blood Mononuclear Cells of Patients with Mixed Cryoglobulinemic Syndrome. J. Virol. 2005; 79(14): 9145-9156.*
Modrow, et al. Computer-Assisted Analysis of Envelope Protein Sequences of Seven Human Immunodeficiency Virus Isolates: Prediction of Antigenic Epitopes in Conserved and Variable Regions. J. Virol. 1987; 61(2): 570-578.*
Cichutek, et al. Development of a quasispecies of human immunodeficiency virus type 1 in vivo. Proc. Natl. Acad. Sci. USA 1992; 89: 7365-7369.*
Zolla-Pazner and Cardozo. Structure—Function Relationships of HIV-1 Envelope Sequence-Variable Regions Provide a Paradigm for Vaccine Design. Nat Rev Immunol. 2010; 10(7): 527-535.*
Sirois, S. et al., 'HIV-I gp120 V3 Loop for Structure-Based Drug Design', <Current Protein and Peptide Science>, 2005, vol. 6, pp. 413-422.
Claudia Charles-Nino et al.: "Variable epitope libraries: New vaccine immunogens capable of inducing broad human immunodeficiency virus type 1-neutralizing antibody response", <Vaccine>, vol. 29, No. 32, Jul. 1, 2011 (Jul. 1, 2011), pp. 5313-5321.
Keller P M et al.: "Identification of HIV vaccine candidate peptides by screening random phage epitope libraries", Virology, Elsevier, Amsterdam , NL, vol. 193, No. 2, Apr. 1, 1993 (Apr. 1, 1993), pp. 709-716.
Javaherian et al.: "Principal Neutralizing Domain of the Human Immunodeficiency Virus Type 1 Envelope Protei N", Proceedings of the National Academy of Sciences, National Academy of Sciences, US, vol. 86, No. 17, Sep. 1, 1989 (Sep. 1, 1989). pp. 6768-6772.
Pedroza-Roldan C et al: "Variable epitope library-based vaccines: Shooting moving targets", Molecular Immunology, Pergamon, GB, vol. 47, No. 2-3, Dec. 1, 2009 (Dec. 1, 2009). pp. 270-282.
Zehender, et al. Compartmentalization of Hepatitis C Virus Quasispecies in Blood Mixed Mononuclear Cells of Patients with Cryoglobulinemic Syndrome. J. Virol. 2005; 79(14): 9145-9156.

* cited by examiner

*Primary Examiner* — Barry A Chestnut
(74) *Attorney, Agent, or Firm* — Andrew C. Cheng

(57) ABSTRACT

Peptide vaccine that is a mixture of different peptide species, where each species has a number of fixed amino acid residues and a number of randomized residues. The fixed resides are the same amino acid residues at the corresponding positions in each species of the mixture while the randomized residues are randomly any available candidate amino acids chosen by design. The degree of randomization may be also been chosen according to the design under a particular situation. This type of peptide vaccines have shown to be able to induce highly specific antibodies against epitopes that are otherwise difficult to induce antibodies in vitro, for example the GPG triplet in the V3 of HIV-1 gp120.

4 Claims, 13 Drawing Sheets

Specification includes a Sequence Listing.

FIG. 1
(A)
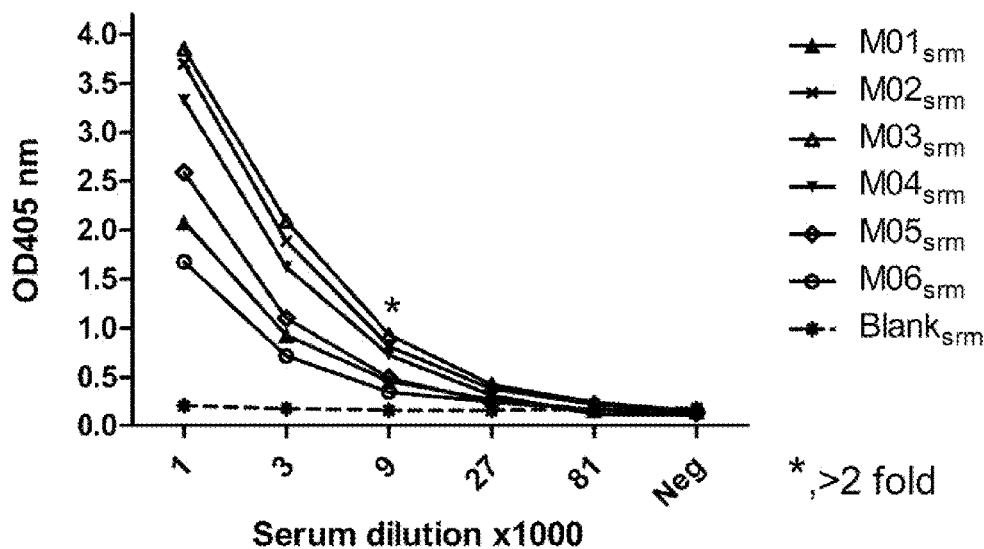
(B)
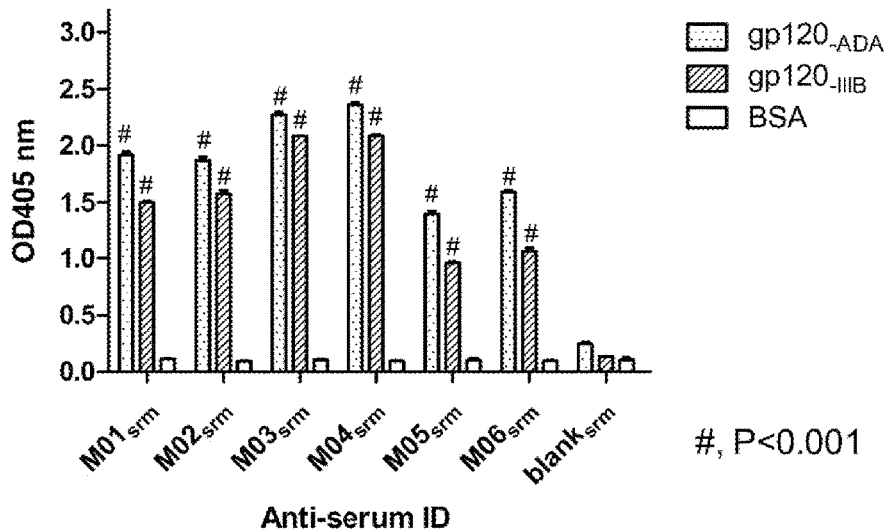

FIG. 6
A
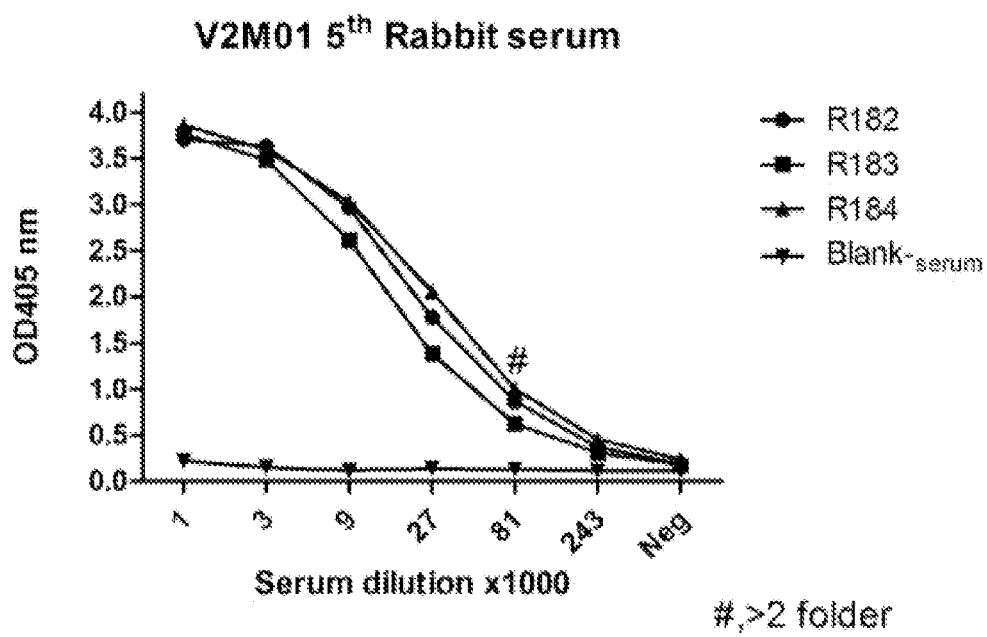
B
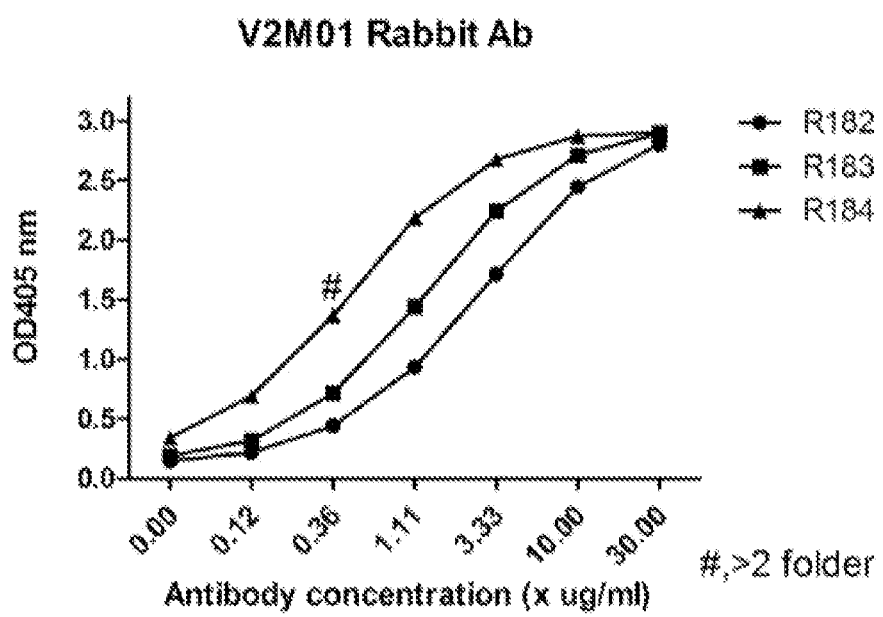

FIG. 7
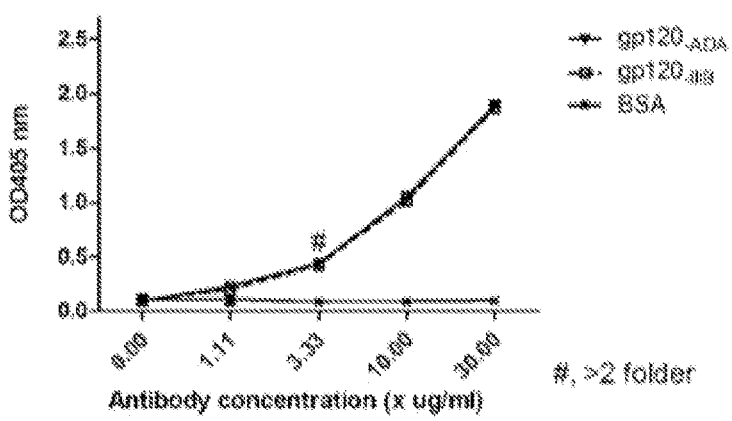
A
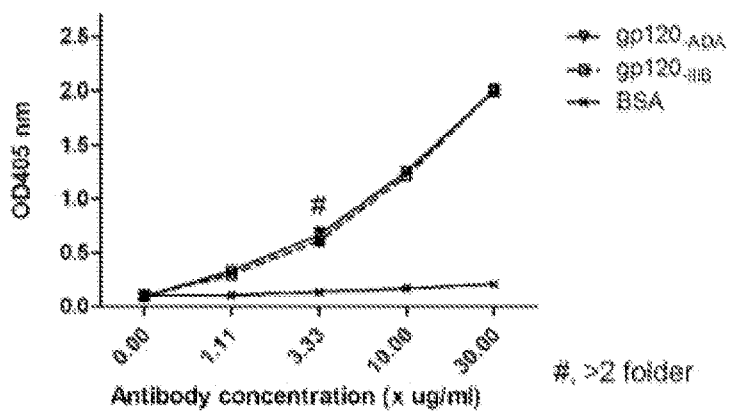
B
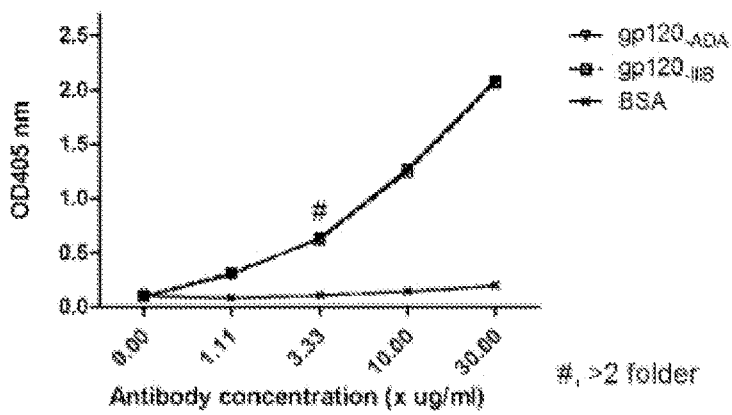
C

FIG. 8
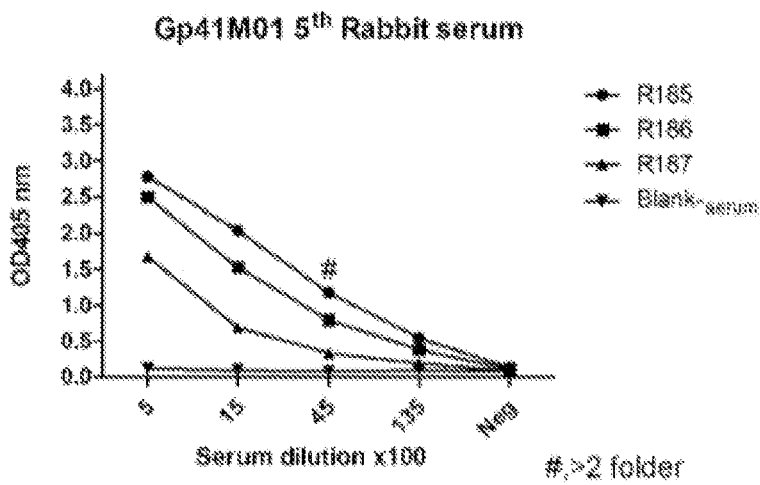
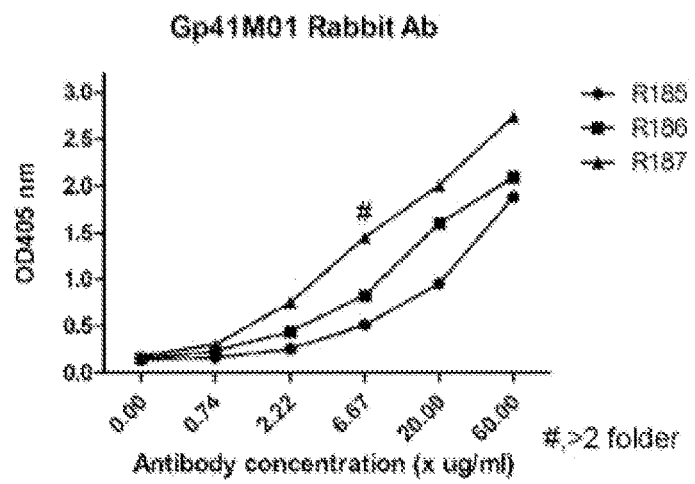
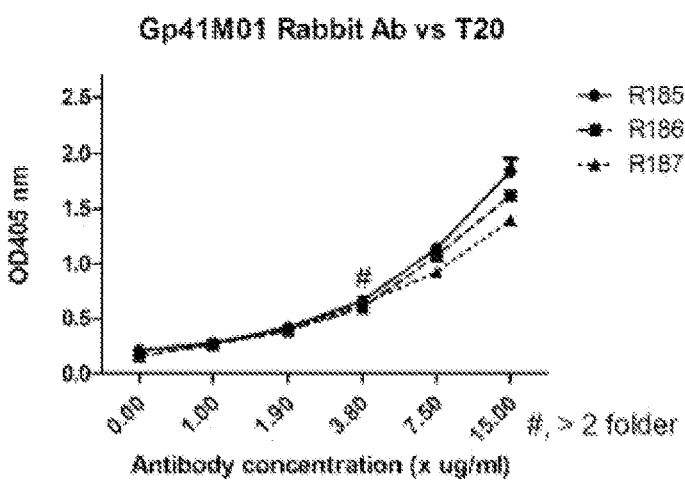

FIG. 9

| Name ID | Sequence | |
|---|---|---|
| V3M01 | XXXXX XGPGX XXXXC | (SEQ ID NO: 1) |
| V2M01 | XXXXX FYXXD XXXXC | (SEQ ID NO: 2) |
| gp41M01 | XXXXX LDXWX XXXXC | (SEQ ID NO: 3) |

FIG. 10 (a)

| clade ID | accession number | clade | coreceptor | V3 tip sequence |
|---|---|---|---|---|
| JR-FL | U63632 | B | R5 | GPGR |
| HXB2 | AF033819 | B | X4 | GPGR |
| CNE1 | HQ699949 | B' | X4 | GPGK |
| CNE6 | HM215423 | B' | R5 | GLGR |
| CNE11 | HM215398 | B' | R5 | GQGR |
| CNE58 | HM215421 | C | R5 | GPGQ |
| CNE16 | HM215402 | B'C | R5 | GPGQ |
| CNE40 | HM215414 | CRF07_BC | R5 | GPGQ |
| CNE23 | HM215408 | CRF08_BC | R5 | GPGQ |
| CNE30 | HM215411 | CRF08_BC | R5 | GPGQ |
| CNE49 | HQ699974 | CRF08_BC | X4 | GPGR |
| CNE3 | HM215410 | CRF01_AE | R5 | GPGQ |
| CNE5 | HM215415 | CRF01_AE | R5 | GPGQ |
| MuLV | AAW21408 | Murine leukemia virus | | |

FIG. 10 (b)

| clade ID | IC50 (ug/ml) | | | | | | |
|---|---|---|---|---|---|---|---|
| | NJU009* | R01* | R02* | R03* | 447-52D | b12 | 4E10 |
| JR-FL | 27.800 | 125.000 | 200.000 | 125.000 | 19.000 | 0.130 | 4.032 |
| HXB2 | 34.000 | 133.333 | 129.870 | 104.712 | 0.737 | 0.119 | 0.175 |
| CNE1 | 15.312 | 200.000 | 187.790 | 176.400 | >50 | >50 | 4.664 |
| CNE6 | >150 | >400 | >400 | >400 | >50 | >50 | 3.520 |
| CNE11 | >150 | >400 | >400 | >400 | >50 | 0.992 | 1.745 |
| CNE58 | 20.571 | 68.965 | 114.000 | 62.500 | >50 | >50 | 4.784 |
| CNE16 | 3.700 | 137.000 | 111.110 | 80.000 | >50 | 3.484 | 7.600 |
| CNE40 | 12.800 | 46.510 | 133.333 | 63.490 | 0.140 | 4.290 | 0.145 |
| CNE23 | 20.000 | 125.000 | 200.000 | 95.230 | >50 | >50 | 9.700 |
| CNE30 | 4.443 | 105.260 | 108.750 | 126.860 | >50 | 4.098 | 25.400 |
| CNE49 | 18.000 | 200.000 | 222.220 | 222.220 | >50 | >50 | 11.490 |
| CNE3 | 24.711 | 166.670 | 172.110 | 180.750 | >50 | >50 | 2.006 |
| CNE5 | 25.000 | 108.110 | 86.960 | 133.330 | >50 | 23.070 | 1.736 |
| MuLV | >150 | >400 | >400 | >400 | >50 | >50 | >50 |

FIG. 10 (c)

| clade ID | ID50 (1/dilution) | | | | | |
|---|---|---|---|---|---|---|
| | M01 | M02 | M03 | M04 | M05 | M06 |
| JR-FL | 62 | 99 | 120 | 104 | 85 | 54 |
| HXB2 | 39 | 45 | 75 | 65 | 53 | 34 |
| CNE1 | ND | ND | ND | ND | ND | ND |
| CNE6 | <20 | <20 | <20 | <20 | <20 | <20 |
| CNE11 | ND | ND | ND | ND | ND | ND |
| CNE58 | ND | ND | ND | ND | ND | ND |
| CNE16 | 189 | 296 | 366 | 316 | 258 | 162 |
| CNE40 | ND | ND | ND | ND | ND | ND |
| CNE23 | ND | ND | ND | ND | ND | ND |
| CNE30 | 120 | 76 | 540 | 200 | 164 | 103 |
| CNE49 | ND | ND | ND | ND | ND | ND |
| CNE3 | 88 | 107 | 193 | 146 | 119 | 75 |
| CNE5 | ND | ND | ND | ND | ND | ND |
| MuLV | <20 | <20 | <20 | <20 | <20 | <20 |

FIG. 12
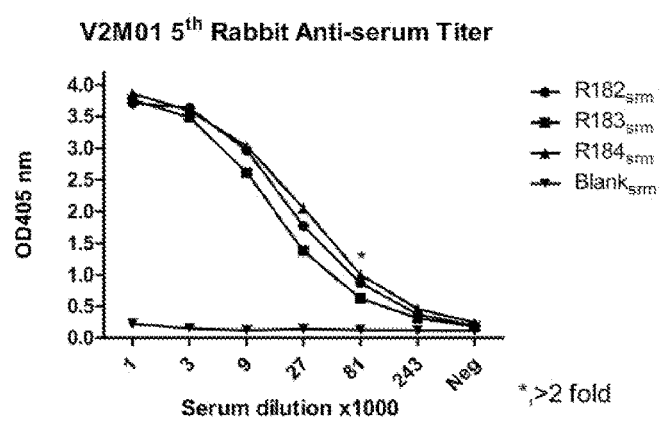
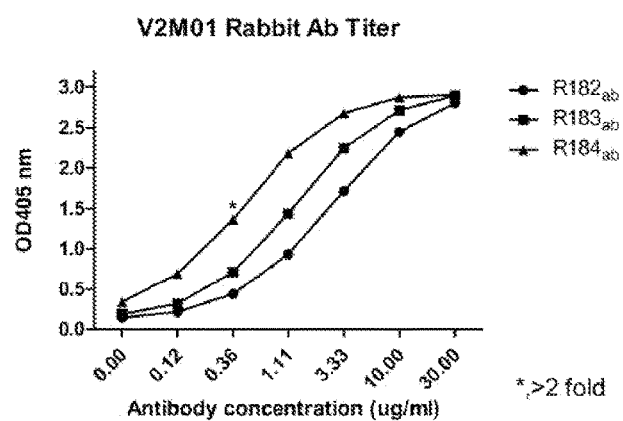
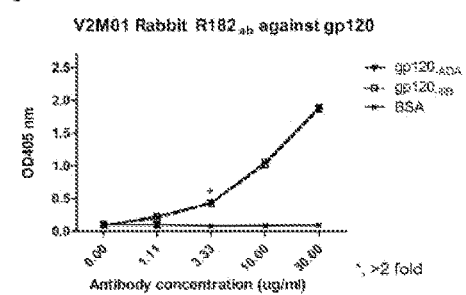
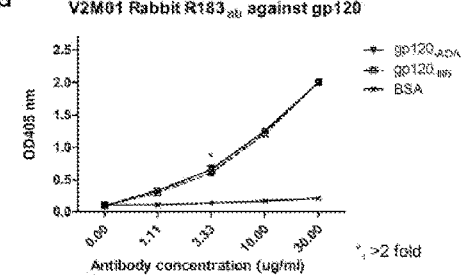
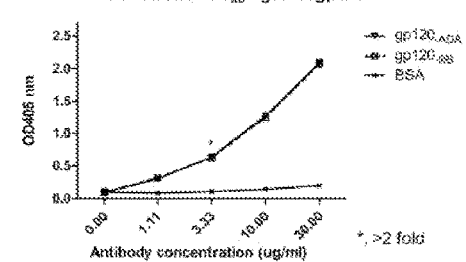

ANTIBODY RECOGNIZING ARBITRARILY DESIGNED EPITOPE OF THREE OR MORE AMINO ACID RESIDUES IN A PEPTIDE AND METHOD OF GENERATING THEREOF

CROSS-REFERENCE TO RELATED APPLICATIONS

This application claims benefit from U.S. Provisional Application No. 61/535,988, filed Sep. 17, 2011, the content of which is incorporated herein in its entirety by reference.

FIELD OF THE INVENTION

The present invention relates to the field of applied immunotechnology. More specifically, it relates to peptide vaccine design or immunogen design for producing antibodies against an epitope of arbitrary sequences, particularly those epitopes against which it is otherwise very difficult to induce antibodies in vitro.

BACKGROUND OF THE INVENTION

Recent advances in the delivery of peptide-based therapeutics have raised new interest in the use of peptide-based vaccines. Synthetic peptides offer several advantages over other forms of vaccines based on inactivated or attenuated microorganisms, including easy production, high safety and low, or even no, detrimental immune responses usually associated with inactivated or attenuated microorganisms. Peptide immunogens have been widely used to induce antibodies with known epitope specificities. Thus, the epitope specificities of the resultant antibodies are determined by the immunologically dominant residues and sometimes also the flank sequences. However, often these antibodies against the immunodominant sequences lack therapeutic importance because those immunodominant epitopes are subject to high degree of mutation in dealing with highly variable viruses, such as HIV, hepatitis C virus (HCV).

In the case of human immunodeficiency virus type 1(HIV-1) infection, the major antibody responses are directed to variable gp120 regions that the virus uses as "decoy" when it mutates and still retains replicating capability. The conserved elements are less immunodominant and do not induce strong antibody response. However, evidence has shown that antibody responses to these conserved elements are critical for containing the virus. Previous studies characterized the third variable (V3) loop of the envelope gp120 as the principal neutralizing determinant (PND) for laboratory T-cell-line-adapted (TCLA) strains of HIV-1. However its amino acid sequence was highly variable so that the mutant resistant to neutralizing antibodies readily arises, thus limiting the potential of targeting this region as a vaccine strategy. Among four residues at the tip of the PND, only the three amino acid residues glycine, proline, and glycine (GPG) in the crown are highly conserved while the fourth residue is variable; A comparison of more than 2000 HIV-1 envelope sequences has shown that more than 95% of their V3 sequences contain the GPG motif while the fourth residue is variable with R in 34%, Q in 54% and K in 4% of the sequences. Functional studies have demonstrated that the PND is a major determinant of viral tropism and a single amino acid substitution within the motif can abrogate viral infectivity in SupT1 and CEM cells, suggesting the conservation of this specific sequence being critical to viral functionality. Serological studies of naturally infected patients have so far only identified antibody specific to all four residues and various reported immunization studies have not shown the ability to induce antibodies specific for the GPG sequence in the PND, regardless of the immunogens used in those studies, such as virus like particle (VLP), recombinant gp120 and peptides, or different immunization strategy taken, such as cocktail peptide, a chimeric virus library Human rhinovirus (HRV), and sequential immunization with V3 peptide. There is no report of antibodies that are specific to GPG itself. Thus, the fact that the critically conversed sequences, such as GPG in the case of HIV, may hold the key to fight against the virus and yet it is so far proved to be difficult to design immunogens for raising the antibodies targeting the GPG motif per se with less concern about mutation, demonstrated the need for novel methods of making vaccines to produce antibodies against the epitope sequences that are not very immunodominant but therapeutically significant, such as the GPG motif.

SUMMARY OF THE INVENTION

An object of the present invention is, accordingly, to provide a novel method of immunogen design for peptide vaccines capable of eliciting therapeutically significant antibodies against virus infection, such as, for example, HIV infection.

Another object of the present invention is to provide a peptide vaccine capable of eliciting production of therapeutically effective antibodies in patients suffering from viral infections.

A further object of the present invention is to provide an antibody with binding specificity dependent only on 3 amino acid residues in the targets. The three residues may be continuous or may be interposed by other residues. As particular embodiment of the invention, it is to provide an antibody that is specific to the GPG sequence of the third variable (V3) loop of the envelope gp120.

These and other objects of the present invention have been realized with the use of the motif immunogen. The motif immunogen is a population or library of short peptides that comprise some fixed amino acid residues and some randomized residues. The fixed residues are those shared by substantially all the peptide species across the library at the corresponding position while the randomized residues can be randomly any amino acid residues. The fixed residues can be continuous in sequence or they can be interposed by one or more randomized residues. The sequence of fixed residues are predetermined according to the intended epitope against which one wishes to raise specific antibodies. Preferably, the motif immunogen comprises a segment of fixed residues flanked by a segment of randomized residues in each side (FIG. 1). One preferred length for the immunogen is 15 residues but other lengths shall also provide satisfactory results, for example, within the range between 10 and 50. Nonetheless the present invention is not limited to any particular length of motif immunogens. The synthesis of the motif immunogen can be performed by conventional methods available in the art, which can be made commercially, and thus is not part of the present invention.

While not willing to be bound by any particular theory, the inventors believe that by randomizing the residues other than those constituting the intended epitope motif it gives the motif residues significant advantages in competition for immunodomance because the entire or most of the antigen population share the same residues in the motif while all other possible competing epitope residues are marginalized due to dilution by sequence randomization. In this way, there is no other epitope in the peptide antigen that can compete with the designated epitope motif even if the later has weaker antigenicity. Therefore by the motif immunization strategy of the present invention, it is possible to induce antibodies against any epitope constituted by any kinds of amino acid sequences, because the motif immunization can let the immunity system focus on the designated target epitope and induce the therapeutically relevant antibodies even which is not present in the human beings or normal animal serum. It must be emphasized, as it would be readily understandable to people of ordinary skill in the art, that the degree of randomization of the flanking sequence may be adjusted according to user's particular situation. While randomizing with all available natural or man-made amino acids seems to be preferable, it shall also provide satisfactory results in given situations with less randomization. For insistence, the particular embodiments disclosed herewith were carried out with 20 nature occurring amino acids. One can imagine that with less than the 20 amino acids or with addition of man-made ones the present invention may also achieve the intended effect: enhancing the intended epitope's antigenicity while minimizing other competing epitopes' immunodominance. For example, if one residue is randomized with 20 available candidates, the library would have 20 difference species, and with 2 such randomized residues, the result would be 400. Then with 3 residue randomization, the different species would be 8000. If the residue is randomized with 10 candidate, the number of species in the library would be 10, 100, and 1000 respectively. Under a given specific situation, it would be within ordinary skill in the art to make changes in the proportion of specific amino acids in designing and synthesizing the peptides to modulate the composition and immuno property of the randomized sequences to achieve different immunological responses or the antibody specificities. It would be also within ordinary skill in the art to conjugate one or more than one of the constant amino acids to generate glycopeptide for the induction of glycan-specific antibodies or antibodies specific for glycan-peptide conformation, or to modify the amino acids by other means, such as sulfation, for the induction of antibodies with unique specificity. In addition, by introducing nonconventional amino acids into the randomized region of a peptide, one may significantly increase the stability of the peptide, thus improving its therapeutic or antibody induction activity. By the same token, the fixed residue needs not to be absolute either. While it is preferable to have the entire library share the same amino acid residue at a fixed position, it is understood that if a certain percentage of the species in the library shares an identical amino acid residues at given position it would be sufficient to give the designated motif residues enough advantage to achieve intended effect. In sum, the present invention is not limited by the degree of the randomness nor by the degree of the fixedness of the randomized residues and fixed residues, respectively. Both can be predetermined or adjusted according a given situation based on the spirit of the present invention, that is, to provide some degree randomness to some residues and some degree of fixedness to other residues to give the later the advantage in terms of immunodominance (or antigenicity).

As a particular embodiment of the present invention, there is provided a peptide vaccine with the GPG motif as the intended epitope motif which is capable of eliciting production of antibodies in mammals with specificity depending solely on the GPG per se without being inuenced by any anking sequences, a type of antibodies that could not be made in all previously known research reports. This particular peptide vaccine is a 15-mer peptide antigen library following the design pattern XXXXX XGPGXXXXXC (SEQ ID: 1) as shown in FIG. 9. This peptide vaccine, referred to as V3MOI in the present invention, were generated by conventional synthetic means. After Balb/c mice were immunized with the peptide vaccine, the result showed that high titer serum antibodies against GPG motif in mice. Hybridoma was generated and a number of monoclonal antibodies were isolated. Immunological characterization of the antibodies demonstrated that the Mabs (monoclonal antibodies) specifically recognized GPG and are capable of neutralizing genetically diverse HIV-1 isolates that carry the GPG sequence, in a pseudovirus assay. Thus, the novel peptide vaccine of the present invention has demonstrated the capability of inducing anti-serum which broadly inhibits various pseudovirus of HIV containing the sequence of GPG in the V3 loop, a motif which is highly conserved with weak immunogenicity. Apart from this particular embodiment, however, it should be understandable to people of ordinary skill in the art that the invention is readily applicable to designing other motif peptide vaccines capable of eliciting therapeutically relevant antibody responses specific to epitope motifs that are of low antigencity and cannot otherwise elicit therapeutically relevant antibody responses using existing methods in the art.

The present invention also provides a therapeutic method that includes a step of (a) manufacturing said peptide vaccine and (b) administering an therapeutically effective amount of said peptide vaccine to the human patients suffering from viral infection.

The present invention further provides an antibody, possessing an epitope binding specificity solely dependent on 3 amino acid residues and not substantially influenced by another amino acid residues flanking or interposing the designated 3 amino acid residues. A particular such antibody has GPG as the designated amino acid residues, which is useful in fighting with the HIV virus.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF THE DRAWINGS

FIG. 1 is a characterization of the murine anti-serum following the fifth immunization with motif antigen V3M01 according to the present invention. A: Elisa test of the titer of the anti-serum, where M01-M06 identify the mouse and the blank-serum refers to the murine serum not immunized with V3M01; X-axis indicates the serum dilution multiply by 1000 so that the value of 1 means the serum is diluted by 1000 times; B: Murine anti-serum binding with gp120 protein of different subtype HIV, (# means OD405 nm of binding with gp120 shows statistic significant higher than its binding with control protein of bovine serum albumin).

FIG. 6 is a characterization of the rabbit anti-serum (A) and Protein G purified poly-antibody (B) following the fifth immunization with V2M01 expressing the V2 sequence of HIV-1 according to the present invention.

FIG. 7 shows the interacting with gp120 of poly-antibodies induced by V2M01 from three rabbits R182, R183 and R186 (A, B, and C, respectively).

FIG. 8 is a characterization of the rabbit anti-serum and purified poly-antibody following the fifth immunization with motif antigens according to the present invention, showing Elisa test of the titer of anti-serum with Gp41M01 (A), poly-antibodies purified by Protein G with Gp41M01 (B), and poly-antibodies purified by Protein G with T20 of gp41(C).

FIG. 9 shows the amino acid sequence patterns as peptide vaccine design used in the exemplary embodiments of the present invention. X: randomized amino acid residue and other letters are one-letter codes of amino acids.

FIG. 10 is the information on env clones and their neutralization sensitivity to bnmAb in the context of pseudotyped viruses, where the concentration of antibody is the total antibody of the anti-serum of ascites purified by Protein G. The Nab concentration or titer is reported as the reciprocal of the purified antibody concentration or the dilution of the plasma that produces 50% inhibition of target cell infection. The negative control is the inhibition of MuLv infection. ND: not determined due to inadequate serum.

FIG. 12 shows antibody responses of an exemplary peptide vaccine V2M01 which follows the design pattern FYXXD, where the fixed residues FYD are interposed by some randomized residues indicated by XX.

DETAILED DESCRIPTION OF PARTICULAR EMBODIMENTS OF THE INVENTION

Construction of Immunogen

Figure 2:
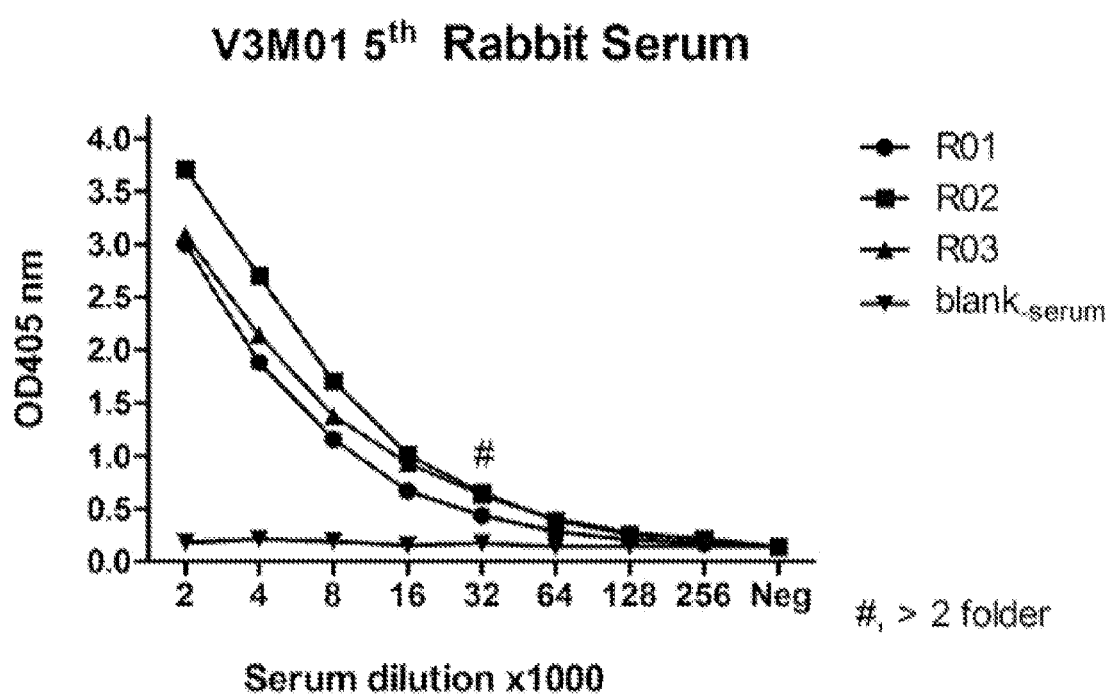
FIG. 2 is a similar characterization as FIG. 1 but it with the rabbit anti-serum following the fifth immunization with V3M01, instead of the murine counterpart, where R stands for rabbit, and 01-03 are serial numbers for each of the three rabbits, respectively (using immunogen as the antigen).
Figure 3:
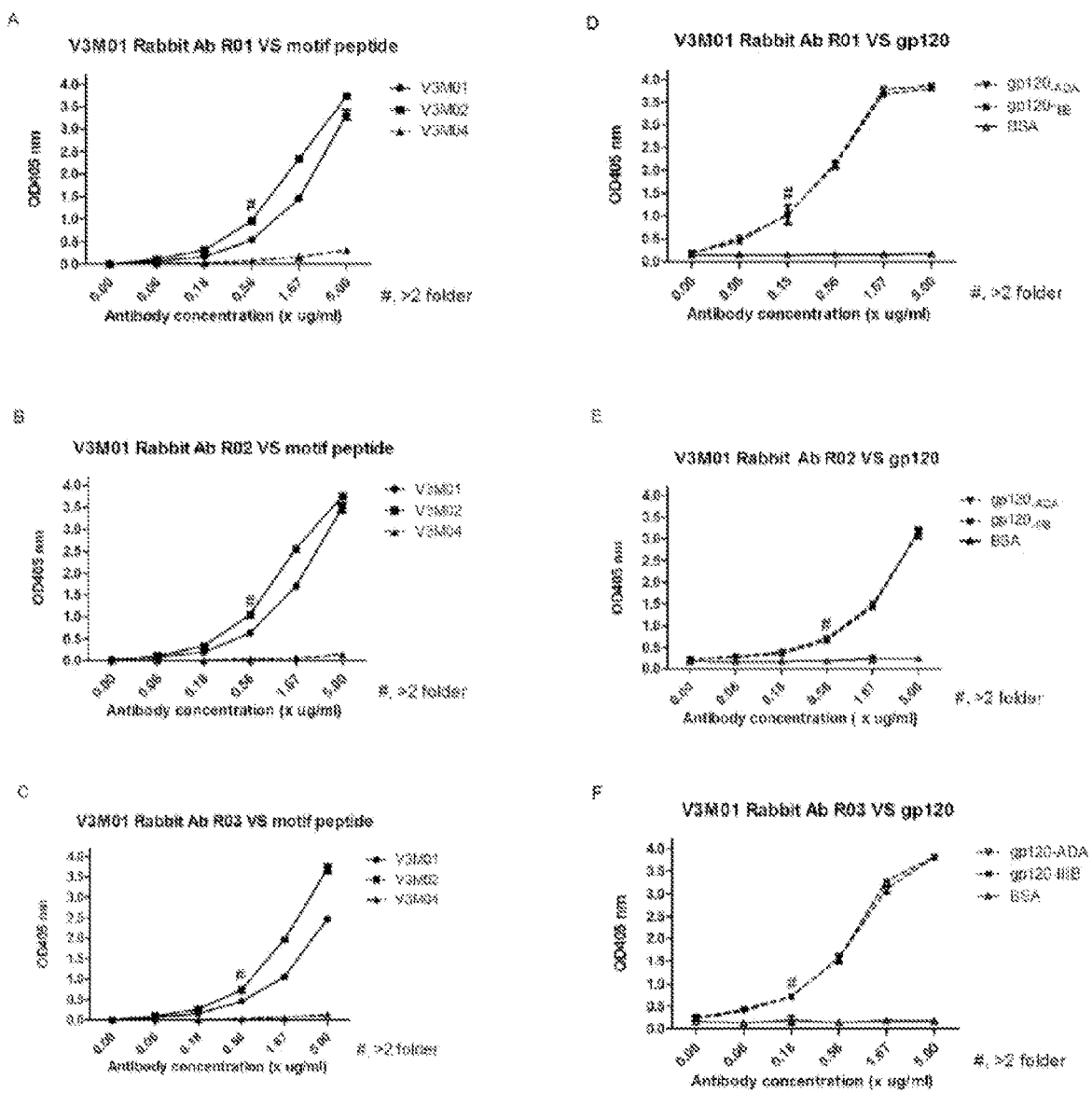
FIG. 3 is a characterization of rabbit anti-serum after the fifth immunization with V3M01 in terms of its interacting with the motif peptide (A, B, and C for three individual rabbits respectively) and gp120 protein (D, E, and F, for three individual rabbits respectively).

The sequence of the immunogen motif peptide library (or novel peptide vaccine) designed as a particular example of the present invention is shown in FIG. 1, where X represents a randomized amino acid residue which can be any amino acid except cystein. The motif peptide library were commercially synthesized in GL Biochem (Shanghai.LTD. China). The Cys (underlined) on the C-terminal was added for conjugation purposes. Each peptide was chemically linked to carrier protein Keyhole Limpet Hemocyanin (KLH, obtained from Sigma, USA), and V3M01 was also conjugated to bovine serum albumin (BSA; obtained from Sigma, USA) as test antigen in ELISA.

Immunization of Mouse and Rabbits

The mice (n=6) were immunized subcutaneously: 100 ul vaccine peptide (1 mg/ml with the conjugate) in PBS and 100 ul complete Freund's adjuvant (CFA, 1:1 ratio) (purchased from Sigma, USA) at a final volume of 200 ul. Boosters were given with 50 ul 1 mg/ml vaccine peptide (in the conjugate) in PBS with 50 ul incomplete Freund's adjuvant (IFA) per mice (purchased from Sigma) at weeks 2, 5 and 8. Anti-sera were then separated for detection. Each group (n=3) of rabbits were immunized with the similar procedure, each with 500 ul 1 mg/ml vaccine peptide (in the conjugate) with 500 ul CPA at the first immunization at week 0 and 500 ul 1 mg/ml vaccine peptide (in the conjugate) with 500 ul IFA at each of the subsequent booting immunization at weeks 2, 5, 8 and 11. Blood was taken from each animal one week after each vaccination event for immune samples (i.e., at weeks 1, 3, 6, 9 and 12). Antibodies were further purified from the murine and rabbit anti-serum samples via Protein G affinity chromatography.

Production of mAbs

Epitope-specific mAbs (monoclonal antibodies) were prepared according to the standard hybridoma technique. Specifically spleen cells from Balb/c mouse were fused with mouse myeloma cells (SP2/0). Antibodies were purified from the ascites of Balb/c mice by affinity chromatography. The isotype of monoclonal antibody was tested with the mouse Monoclonal antibody isotyping reagents (077K4825, from Sigma, USA).

Detection of Peptide-Specific Antibodies in ELISA-Assay

The peptide-specific antibodies in the murine and rabbit anti-serum samples obtained in the above were tested in the enzyme-linked immunosorbent assay (ELISA-assay). Recombinant gp120s were purchased from ImmunoDiagnostics, Inc. (Woburn, Mass., USA) or from the NIH AIDS Reagent Program (Bethesda, Md., USA), peptides of B and B' subtype of HIV were commercially synthesized in GL Biochem (Shanghai, LTD, China). 96-well polyvinylchloride plates (Corning, N.Y., USA) were coated with 100 ul of Bug/ml gp120 or peptide diluted in 50 mM bicarbonate buffer, pH 9.6, and incubated at 4° C. for 16 hours. Unbound peptide or protein was removed by repeated washing with PBS, pH7.4, containing 0.05% Tween-20 (washing buffer). Nonspecific sites were blocked with 200 ul 5% nonfat milk dissolved in washing buffer, at 37° C. for 60 min. 100 ul of murine anti-serum, ascites or rabbit anti-serum or antibody with different dilution in washing buffer were added and allowed to incubate at 37° C. for 60 min. Unbound peptides were removed by repeated washing. The bound antibody were detected with AP-conjugated goat anti-rabbit or goat anti-mousestreptavidin (Pierce, USA) diluted at 1:2000 and measured at 405 nm.

Cloning of Full-Length Envelope Genes and Production of Pseudotyped Viruses

Full-length envelope genes were amplified by PCR directly from proviral DNA extracted from patients' uncultured peripheral blood mononuclear cells. The PCR was conducted with initial denaturation at 94° C. for 2 min, followed by 35 cycles of 94° C. for 15 s, 55° C. for 30 s, and 68° C. for 4 min, followed by a final extension at 68° C. for 10 min. Subtype-specific primer sequences were designed to be as conserved as possible based on the published sequences of geographical variants. PCR-amplified fragments were cloned directly into the pcDNA 3.1 expression vector (Invitrogen) and verified by direct sequencing. Env-bearing pseudotyped viruses were generated by co-transfection of env-expressing plasmid together with backbone construct pNL43R-E-luciferase into the 293 cells. A control plasmid expressing envelope glycoprotein of HIV-1 HXB2, SF162, or JRFL and of amphotropic murine leukemia virus was also included. Forty-eight hours post-transfection, culture supenatant was collected and tested for luciferase activity to standardize viral input in the subsequent functional analysis.

Neutralizing Activity of Anti-Serum and mAb Against Pseudotyped Virus

Neutralizing activities of bnmAb, 4E10, 447-52D, b12, (purchased from Polymun, LTD, USA), pooled plasma samples and purified antibody were jointly analyzed. All plasma samples were heat-inactivated at 56° C. for 1 h before testing. In brief, 200 TCID50 of pseudotyped viruses was incubated with serially diluted anti-sera or monoantibody purified from Protein G, in a 96-well plate in triplicate for 1 h at 37° C. Approximately $1 \times 10^4$ GHOST.CD4/X4/R5 cells stably transfected to express HIV-1 receptor CD4 and co-receptor CCR5 or CXCR4 were then added, and the cultures were maintained for an additional 48 h at 37° C. Neutralizing activity was measured by the reduction in luciferase activity compared with the control. The log 10 ID50 titers were calculated based on the standard algorithm used in the art.

The Titer of Antiserum of V3M01

Following the second immunization, all six animals developed antibody responses. As shown in FIG. 1A, the serum antibody endpoint titers after the 5th immunization reached >10000 in all animals. ELISA analysis of the antiserum antibodies showed that all six animals developed antibodies reacting with both the immunogen and recombinant gp120s of HIV-1$_{IIIB}$ and HIV-1$_{ADA}$ (FIG. 1B). They also neutralized both laboratory adapted and primary HIV-1 isolates. Hybridomas were generated from one of the animals (No. 4) and 6 monoclonal antibodies were isolated. All 6 mAbs exhibited various degrees of broadly neutralizing activities against a panel of viruses.

Characterization of Monoantibody NJU009

Figure 5:
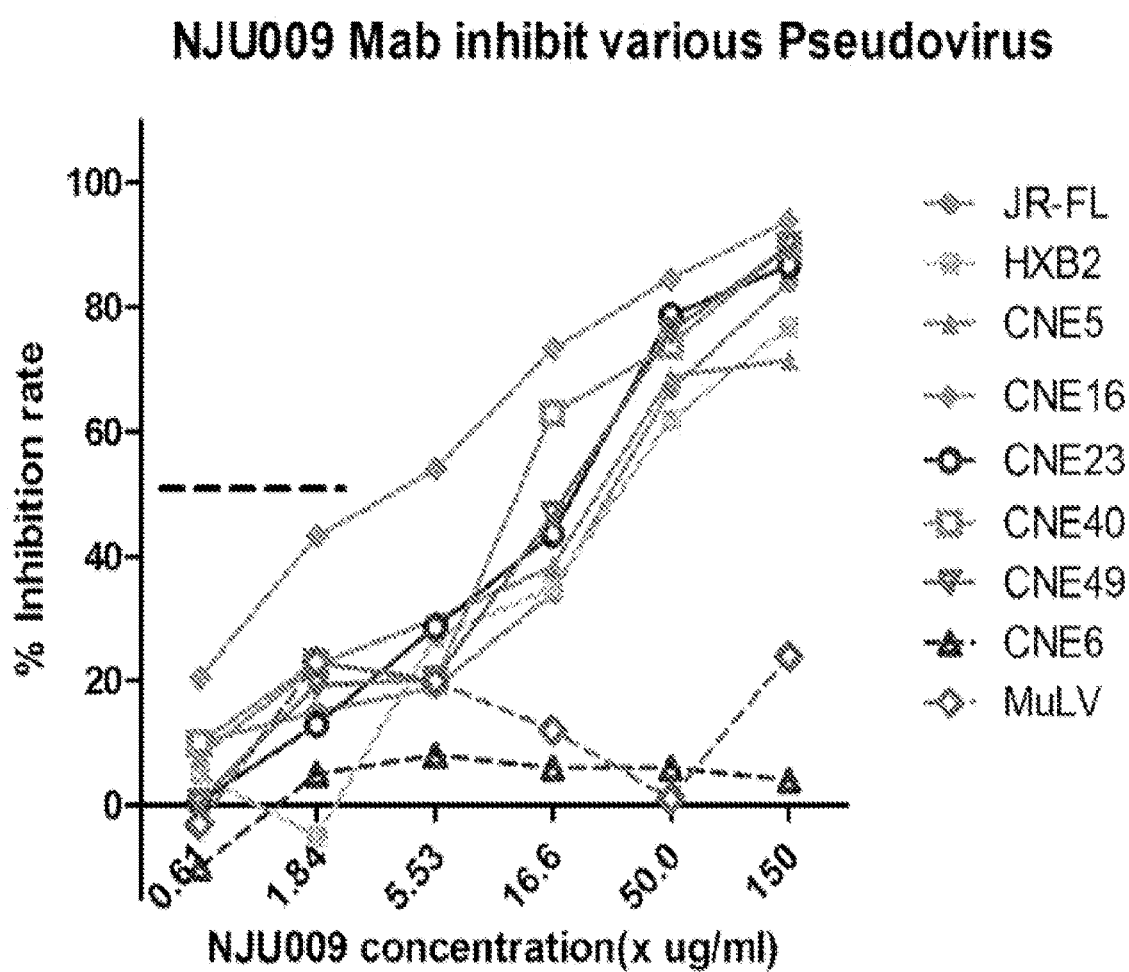
FIG. 5 characterizes NJU009's inhibitory effects on various pseudovirus.

As shown in FIG. 5 and FIG. 10, NJU009, one of the most potent mAbs, was further characterized for its neutralizing activity against a panel of pseudotyped viruses consisting of 11 primary isolates and 2 laboratory strains representing subtypes B, B', C, B'C recombinant, and a number of circulating recombinant forms (CRFs). Eleven out of 13 isolates were neutralized by NJU009 with the ND$_{50}$ ranging from 3.7 ug/ml for CNE16 (B'C) to 20.5 ug/ml for CNE58 (Clade C) with CNE 6 and CNE11 completely resistant to the neutralization by NJU009. The CCR5-using JR-FL, an isolate known for its resistant to V3 antibody neutralization had an ND$_{50}$ of 27.8 ug/ml, and HXB2, a CXCR4 virus, had an ND$_{50}$ of 34 ug/ml. For almost all isolates sensitive to NJU009 neutralization, the curves were tightly clustered, implicating that their neutralization sensitivities were not influenced by the flanks of the GPG epitope. Two isolates, CNE6 and CNE11 (both Clade B') with GLG and GQG in their PND, respectively, completely resisted to NJU009 neutralization. The observation suggested that the NJU009 neutralization activity was specifically mediated by the GPG sequence. The control virus pseudotyped with a MuLV env that enters the cells independent of CD4 and any co-receptors, was not affected by the antibody. 447-52D, one of the V3 mAbs with broadest neutralizing activity against viruses carrying GPGR sequence, potently neutralized HXB2 and JR-FL with ND$_{50}$s of 0.737 ug/ml and 19 ug/ml, respectively. 447-52D also potently neutralized CNE40, a CRF07_BC and the most easily neutralized isolate among the tested panel, with a ND$_{50}$ of 0.14 ug/ml. However, 447-52D failed to neutralize rest of the isolate. b12, specific for CD4 binding site, neutralized 7 out of 13 isolates with ND$_{50}$s ranging from 0.119 ug/ml (HXB2) to 23.07 ug/ml (CNE5). 4E10, one of the most broadly neutralizing mAbs specific for MPER of gp41, neutralized 13 out of 13 isolates.

Epitope Mapping

Figure 4:
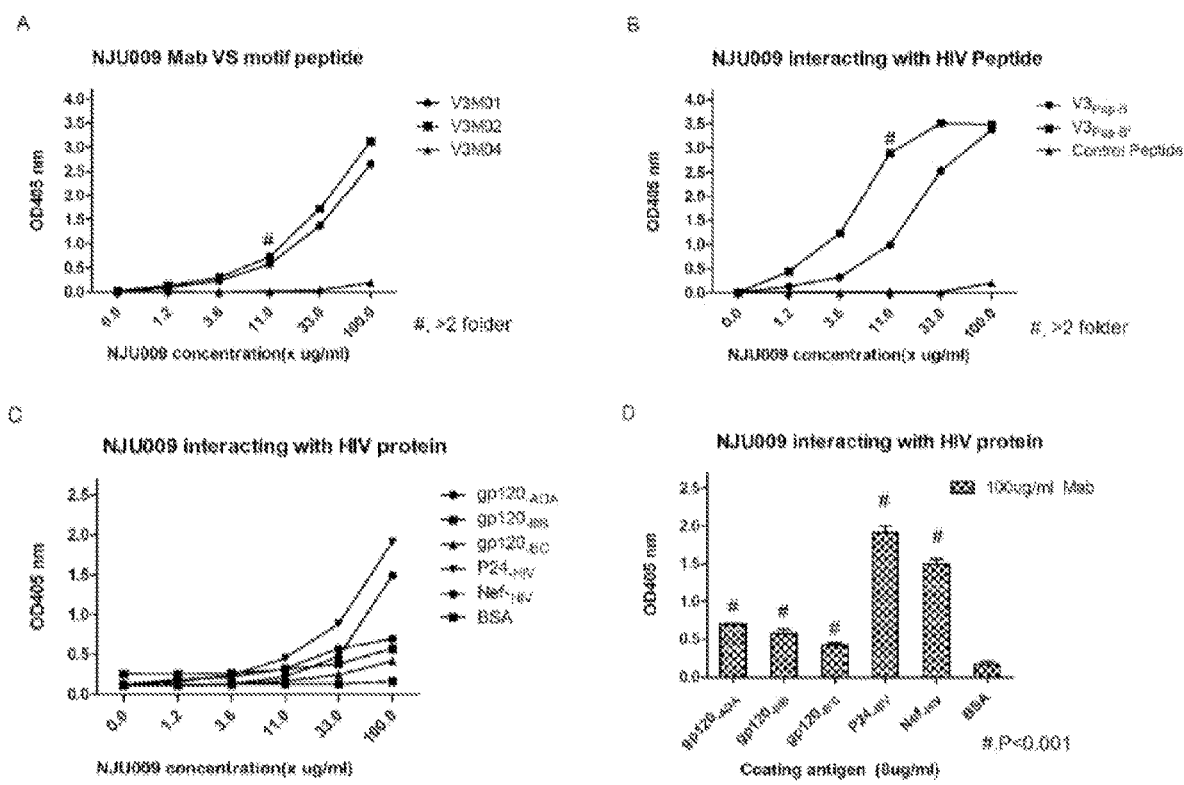
FIG. 4 is a characterization of NJU009 in terms of its interacting with the motif peptide (A), HIV peptide (B), HIV protein (C, D). D is a bar-graph at the concentration of 100 ug/ml NIU009.

To ascertain that the broadly neutralizing activity of NJU009 was indeed mediated by GPG instead of the flank sequence and to characterize the epitope specificity, NJU009 was further analyzed for its binding activity against peptides with the GPG triplet sequence replaced by Ala. The NJU009 binding to the peptides was completely abrogated when the three amino acid residues were replaced with Ala one-by-one or altogether simultaneously (FIG. 2). This suggests that NJU009 is highly specific for GPG and its neutralization activity was mediated specifically by the motif sequence instead of the flank sequences. This conclusion is consistent with the tightly clustered neutralization curves respite of the diverse V3 sequences of the viruses. The absolute dependency on all three amino acid residues by NJU009 also suggests that the three amino acid residues may be in direct contact with NJU009. NJU009 also exhibited comparable recognition of V3 peptides derived from various isolates (FIG. 4) and recombinant gp120s derived from HIV-1 ADA, IIIB and a B'C recombinant isolate. Since the flank sequences of above antigens are distinct, the observation suggested that the NJU009 reactivities were GPG specific and its recognition of the epitope is minimally influenced by the sequences flanking the epitope motif. The IgG genes of variable region were amplified from all six hybridoma clones by RT-PCR. The deduced sequences of amino acid from the nucleotides showed that the amino acid (aa) sequences of heavy chain variable regions are 100% identical for all clones while the aa sequences of light chain variable regions of NJU001, NJU003 and NJU005 are identical, and NJU007, NJU008 and NJU009 are identical, suggesting that NJU001, 003 and 005 were likely derived from the same parental hybridoma clone and NJU007, 008 and 009 from another clone. The majority of the differences are concentrated in the CDR regions and the C-terminus of the VL region.

NJU009 and 447-52D recognize the tip of the V3 loop with only one amino acid residue difference. A competition study was performed between NJU009 and 447-52D to further investigate the epitope specificity. The competition curve showed bi-phasic property with 6.25 ug/ml 447-52D as a transition point (FIG. 2). At concentrations below 6.25 ug/ml 447-52D, NJU009 binding to gp120 was competed by increasing concentrations of 447-52D in a dose-dependent manner up to approximately 85%. However, the remaining 15% NJU009 binding activity was much less sensitive to the presence of 447-52D, requiring a 15-fold more 447-52D to reach complete inhibition. This data indicate that the epitope of NJU009 partially overlapped with that of 447-52D, and with about 10% NJU009 binding activity relatively insensitive to the presence of high concentration 447-52D.

Inducibility and Animal Specificity

To demonstrate whether the anti-GPG antibodies were readily inducible and to determine serum antibody concentrations, rabbits were immunized with V3M01 and sera were collected after the serum antibody titers reached plateau. The result showed that the immunogen also induced strong antibody responses in rabbits and had comparable binding reactivities against recombinant gp120s derived from HIVADA, IIIB and a B'C recombinant isolates (FIG. 3). The sera exhibited similarly broadly neutralizing activities and the antibody specificities were similarly mapped to the GPG sequence, suggesting that the induction of the antibodies to such an antigen is readily achievable and not animal species restricted.

Broad Applicability of the Motif Immunization Methodology

Figure 13:
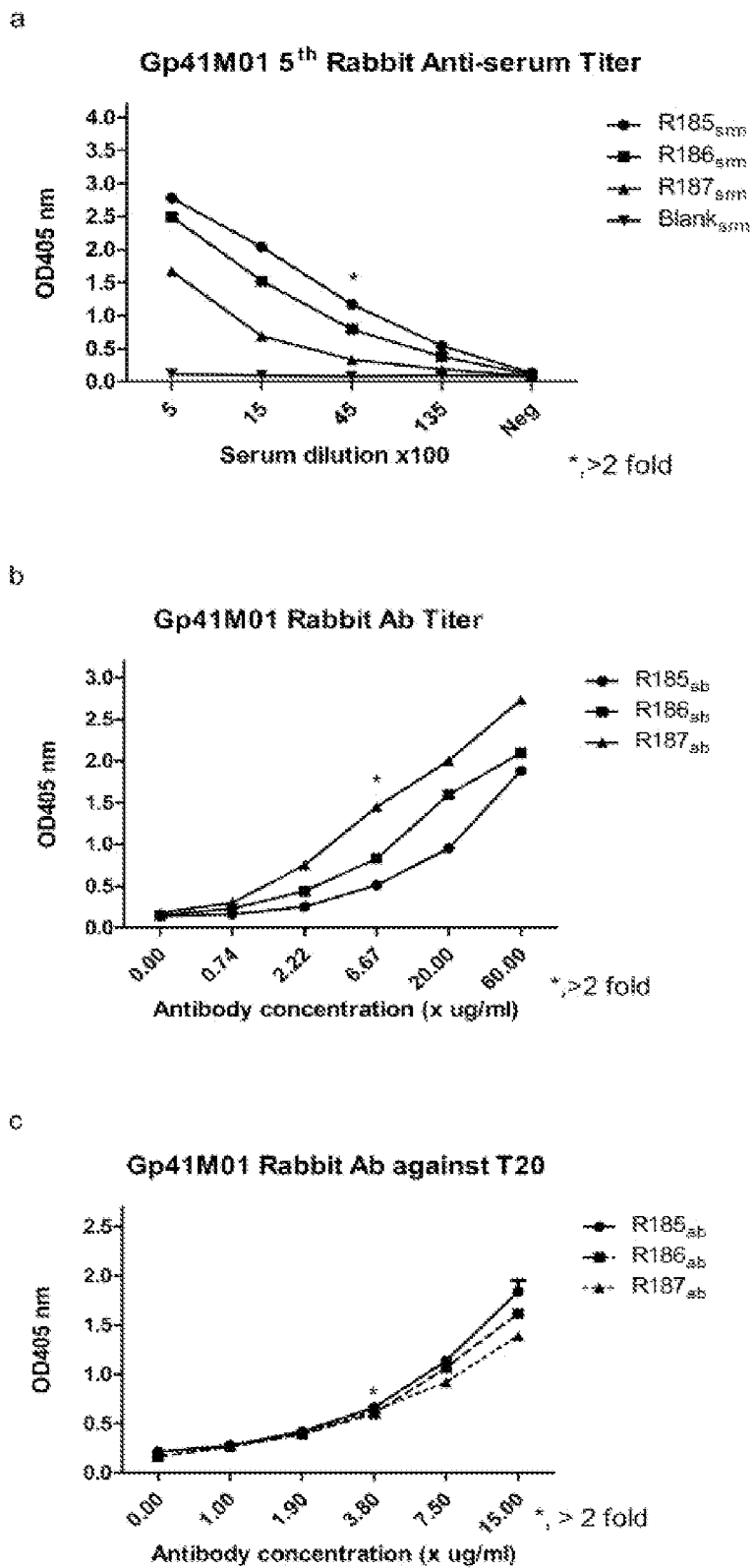
FIG. 13 shows antibody responses of another exemplary peptide vaccine Gp41M01 which follows the design pattern LDXW, where the fixed residues LDW are interposed by a randomized residue indicated by X.

To demonstrate the applicability of the targeted induction of antibodies of the Motif Immunization Methodology of the present invention is not limited to the GPG motif but can be applied to other sequences as well, a number of HIV-1 gp120 sequences were selected, which are known to contain or be part of antigenic epitopes but hard to induce its specific antibodies using conventional strategies. The V1V2 region, for example, is known to contain epitopes that mediate cross neutralizing activities but to which few such antibodies were successfully induced. A sequence of FYXXD (SEQ ID NO: 7) in the V2 crown was selected as the immunogen for a number of reasons: (1) recently two broadly neutralizing mAbs, PG9 and PG16, isolated from an HIV-infected human and mapped to V2 and V3, showed that alanine replacement of F176 increased the IC50s for more than 5000 and 7000 folds, respectively, and (2) the aspartic acid (D) is part of the LDL binding sequence for integrin 47, the gut mucosal homing receptor for peripheral T cells. Since the lysine (K) and leucine (L) are poorly conserved among HIV-1 isolates, only the highly conserved FY and D (93, 91 and 96% conservation, respectively) were included in the construction of the epitope according to the present invention. A 15-mer peptide library was synthesized with two AA spacings between Tyrosine and Aspartic acid. All three rabbits immunized with the peptide developed strong antibody responses, reaching endpoint titers of >80000 after 5th immunization (FIG. 12, FIG. 9). Characterization of the serum antibodies demonstrated that the serum antibodies reacted with gp120ADA, gp120BC and gp120mB. The serum antibodies were also reactive with V2 recombinant glycoproteins. However, this V2 antibody did not demonstrate appreciable neutralization activity. The membrane proximal external region (MPER) of gp41 contains a number of highly conserved epitopes recognized by broadly neutralizing mabs, such as 2P5 and 4EIO. Both mAbs were isolated from infected individuals and repeated efforts to induce such antibodies have met with failure. The 2P5 epitope ELDKWA (SEQ ID NO: 5) contains three highly conserved residues with L663, D664 and W666 at 98, 97 and 99% usage frequency, respectively. A 15-mer peptide containing LDXW (SEQ ID NO: 6) sequence induced antibody responses that recognized T20 (FIG. 13, FIG. 9).

Figure 11:
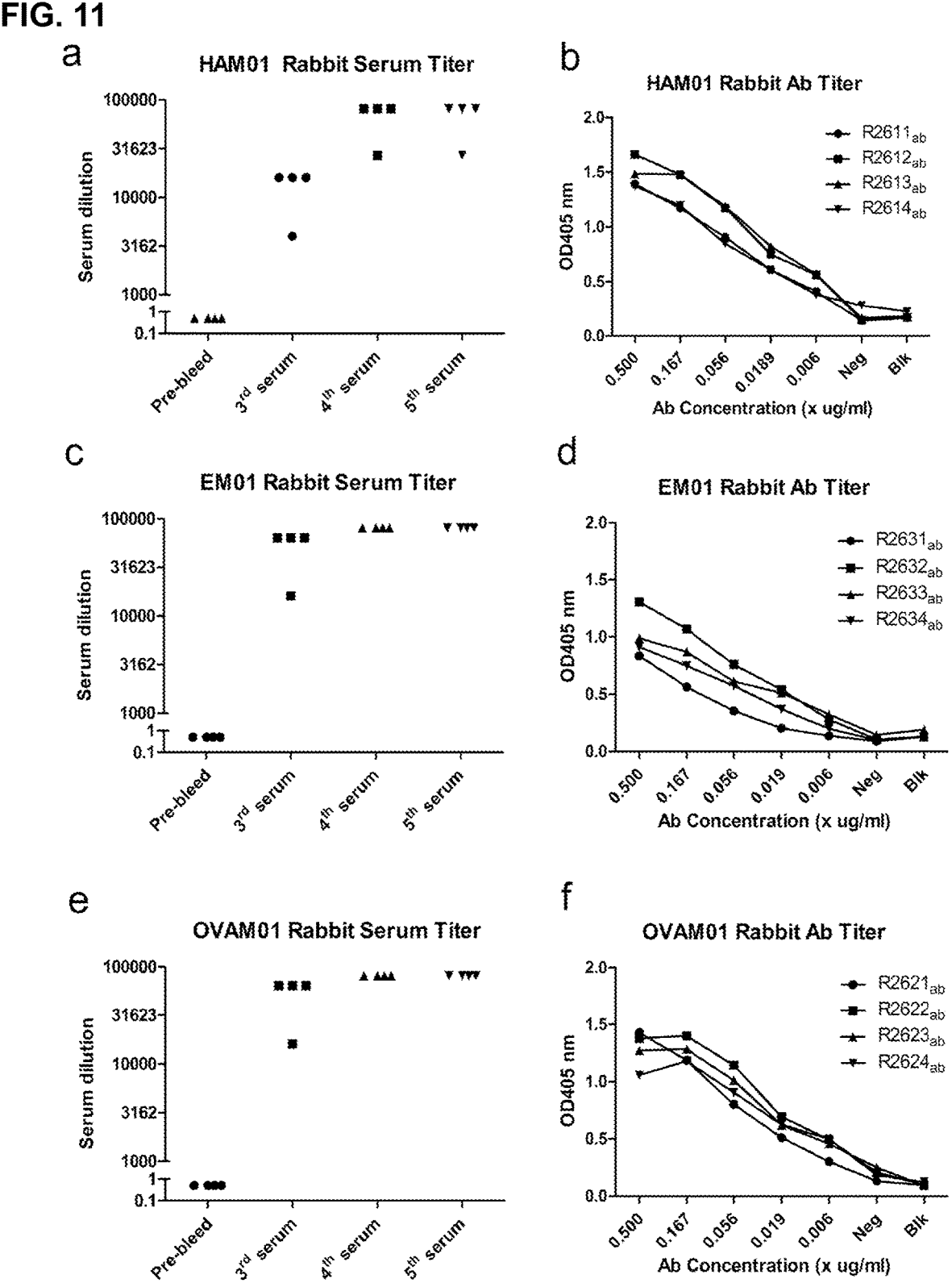
FIG. 11 shows the titer of the anit-serum elicited by three different peptide libraries HAM01, EM01 and OVAM01 which were designed according to the present invention, with HAM01 representing a conserved sequence in several influenza viruses and EM01 representing a conserved sequence in HCV.

Based the above results, it is believed that using this targeted antibody induction technology of the present invention to design peptide vaccines, it is possible to induce antibodies to sequences of no known antigenicity or even arbitrary sequences. As shown in FIG. 11, we designed three peptides, HAM01, EM01, and OVAM01, containing sequences derived from influenza virus, HCV and OVA, respectively. HAM01 contained triplet residues HHP derived from aa199-201 located within the receptor-binding subdomain of HA1 and are highly conserved among different IFV subtypes and IFVs from different species. EM01 contained triplet residues HRM derived from highly conserved aa316-318 located in the E1 protein of HCV. None of the epitopes have documented antibodies though S139/1, a broadly neutralizing mAb, was mapped to a conformational epitope within the HA1 subdomain of IFV, consisting of residues of both upstream and downstream of HHP. OVA01 contained ERK of a 276-278 in OVA. All three peptides induced high titer serum antibodies reacting with the immunogens.

While not being part of the invention, the inventors' hypothesis is that this epitope design strategy of the present invention allows the selected epitope prominently recognizable to the immune system and minimizes the inuence of the side chains in the sequence. The GPG antibody is unique in that none of the HIV-1 infected individuals in the panel had serum antibodies reacting with the GPG peptide while a number of sera reacted with peptides expressing GPGR (SEQ ID NO: 4) or GPGQ (SEQ ID NO: 8), suggesting that the GPG sequence is not recognized by the host's immune system during natural infection, or alternatively the B cell clones recognizing GPG were minor clones and became de-selected during the clonal expansion. Mechanistic studies indicated that the immunodominant GPGR (SEQ ID NO: 4) (or GPGQ (SEQ ID NO: 8) or K) may dominate over the none dominant GPG during clonal expansion and the later eventually became de-selected in natural infection. NMR studies have determined the interactions of a number of V3 mAbs with V3 peptides. 0.5, a type specific V3 mab, binds to the V3 peptide through 16 amino acid residues while 447-52D, one of the most broadly cross neutralizing mab, interacted with V3 peptide through multiple interaction. In addition to GPGR(SEQ ID NO: 4) contact, 0.5 also has direct interactions with 16 side chain residues of the peptide (RP135), likely contributing to both the affinity and the binding rigidity. NJU009 may have much more binding flexibility than both V3 antibodies since it does not interact with any ank sequences in its binding to the V3, which may at least partially account for its broadly neutralizing activity.

In sum, it is believed that the present invention is of important therapeutic applications in terms of peptide vaccines. Additionally, one could also incorporate arbitrary sequence into a polypeptide or protein as either a detection or purification tag The Anti-Serum of V2M01 and gp41M01

FIGS. 6A and 8A shows that the rabbits immunized with V2M01 and gp41M01 produced specific anti-serum against motif immunogen. Furthermore, the anti-serum of V2M01 was also shown to bind with different gp120 with the sequence pattern, FYXXD, in accord with the motif of V2M01 (FIG. A-D). Additionally, the anti-serum of gp41M01 showed high affinity with T20 peptide of gp41, which was made up with the specific amino acid sequence, LDXW, identical to immunogen of gp41M01 (FIG. 8B).

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims. It is further understood that the present invention can be practiced even without referring to these specific examples because the essence of the present invention does not lie in technical difficulty or complexity but in the novel ideas itself. Once the idea is known, the practice of it is within ordinary skill in the art.

What is claimed is:

1. An immunogenic composition, comprising a mixture of peptides each comprising a sequence as SEQ ID NO:1, with three fixed amino acid residues of GPG flanked by randomized amino acid residues X on each side,
wherein the length of the peptides is between 10 and 50 amino acids, and the number of said randomized amino acid residues is 11.

2. The immunogenic composition of claim 1, wherein the immunogenic composition is used for treating viral infection, and said viral infection is caused by HIV.

3. The immunogenic composition of claim 1, wherein said mixture of peptides comprises at least 400 different species.

4. The immunogenic composition of claim 3, where said mixture of peptides comprises at least 8000 different species.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial
<220> FEATURE:
<223> OTHER INFORMATION: synthetic peptide library
<220> FEATURE:
<221> NAME/KEY: VARIANT
<222> LOCATION: (1)..(6)
<223> OTHER INFORMATION: Xaa can be any naturally occurring amino acid
<220> FEATURE:
<221> NAME/KEY: VARIANT
<222> LOCATION: (10)..(14)
<223> OTHER INFORMATION: Xaa can be any naturally occurring amino acid

<400> SEQUENCE: 1

Xaa Xaa Xaa Xaa Xaa Xaa Gly Pro Gly Xaa Xaa Xaa Xaa Xaa Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic peptide library
<220> FEATURE:
<221> NAME/KEY: VARIANT
<222> LOCATION: (1)..(5)
<223> OTHER INFORMATION: Xaa can be any naturally occurring amino acid
<220> FEATURE:
<221> NAME/KEY: VARIANT
<222> LOCATION: (8)..(9)
<223> OTHER INFORMATION: Xaa can be any naturally occurring amino acid
<220> FEATURE:
<221> NAME/KEY: VARIANT
<222> LOCATION: (11)..(14)
<223> OTHER INFORMATION: Xaa can be any naturally occurring amino acid

<400> SEQUENCE: 2

Xaa Xaa Xaa Xaa Xaa Phe Tyr Xaa Xaa Asp Xaa Xaa Xaa Xaa Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide library
<220> FEATURE:
<221> NAME/KEY: VARIANT
<222> LOCATION: (1)..(5)
<223> OTHER INFORMATION: Xaa can be any naturally occurring amino acid
<220> FEATURE:
<221> NAME/KEY: VARIANT
<222> LOCATION: (8)..(8)
<223> OTHER INFORMATION: Xaa can be any naturally occurring amino acid
<220> FEATURE:
<221> NAME/KEY: VARIANT
<222> LOCATION: (10)..(14)
<223> OTHER INFORMATION: Xaa can be any naturally occurring amino acid

<400> SEQUENCE: 3

Xaa Xaa Xaa Xaa Xaa Leu Asp Xaa Trp Xaa Xaa Xaa Xaa Xaa Cys
1               5                   10                  15

<210> SEQ ID NO 4
<211> LENGTH: 4
<212> TYPE: PRT
<213> ORGANISM: human
```

```
<400> SEQUENCE: 4

Gly Pro Gly Arg
1

<210> SEQ ID NO 5
<211> LENGTH: 6
<212> TYPE: PRT
<213> ORGANISM: human

<400> SEQUENCE: 5

Glu Leu Asp Lys Trp Ala
1               5

<210> SEQ ID NO 6
<211> LENGTH: 4
<212> TYPE: PRT
<213> ORGANISM: human
<220> FEATURE:
<221> NAME/KEY: VARIANT
<222> LOCATION: (3)..(3)
<223> OTHER INFORMATION: Xaa can be any naturally occurring amino acid

<400> SEQUENCE: 6

Leu Asp Xaa Trp
1

<210> SEQ ID NO 7
<211> LENGTH: 5
<212> TYPE: PRT
<213> ORGANISM: human
<220> FEATURE:
<221> NAME/KEY: VARIANT
<222> LOCATION: (3)..(4)
<223> OTHER INFORMATION: Xaa can be any naturally occurring amino acid

<400> SEQUENCE: 7

Phe Tyr Xaa Xaa Asp
1               5

<210> SEQ ID NO 8
<211> LENGTH: 4
<212> TYPE: PRT
<213> ORGANISM: human

<400> SEQUENCE: 8

Gly Pro Gly Gln
1
```